(12) United States Patent
Cooper et al.

(10) Patent No.: US 9,868,981 B2
(45) Date of Patent: Jan. 16, 2018

(54) AMPLIFICATION ASSAY WITH A PROBE COMPETITOR

(71) Applicant: Bio-Rad Laboratories, Inc., Hercules, CA (US)

(72) Inventors: Samantha Cooper, Berkeley, CA (US); Wei Yang, Dublin, CA (US); Jennifer Berman, San Carlos, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/181,173

(22) Filed: Jun. 13, 2016

(65) Prior Publication Data

US 2016/0362731 A1    Dec. 15, 2016

Related U.S. Application Data

(60) Provisional application No. 62/174,279, filed on Jun. 11, 2015.

(51) Int. Cl.
*C12Q 1/68* (2006.01)
*G06F 19/22* (2011.01)

(52) U.S. Cl.
CPC ........... *C12Q 1/6827* (2013.01); *G06F 19/22* (2013.01)

(58) Field of Classification Search
None
See application file for complete search history.

(56) References Cited

U.S. PATENT DOCUMENTS

| | | |
|---|---|---|
| 2004/0142369 A1 | 7/2004 | Alajem et al. |
| 2007/0092880 A1 | 4/2007 | Crothers et al. |
| 2013/0099018 A1 * | 4/2013 | Miller ............... B05B 1/08 239/10 |
| 2013/0323727 A1 | 12/2013 | Huang et al. |

FOREIGN PATENT DOCUMENTS

WO    WO 2014/074651 A1 *   5/2014

OTHER PUBLICATIONS

Zhou et al, BioTechniques 50 (5), 311 (May 2011).*
Jia, Yanwei, "Kinetic Hairpin Oligonucleotide Blockers for Selective Amplification of Rare Mutations", Scientific Reports, Aug. 1, 2014, vol. 4, 8 pages.
Thomas, Shane, Authorized Officer, U.S. Receiving Office, "International Search Report" in connection with related International Application No. PCT/US2016/037259, dated Sep. 14, 2016, 3 pages.
Thomas, Shane, Authorized Officer, U.S. Receiving Office, "Written Opinion of the International Searching Authority" in connection with related International Application No. PCT/US2016/037259, dated Sep. 14, 2016, 10 pages.

* cited by examiner

*Primary Examiner* — James Martinell
(74) *Attorney, Agent, or Firm* — Kolisch Hartwell, P.C.

(57) ABSTRACT

Methods and compositions for detecting an allelic form of a target. In an exemplary method, partitions may be created that collectively contain at least one first allelic form and a second allelic form of a target. Each partition may contain (i) a same probe capable of binding specifically to each of the first and second allelic forms of the target and (ii) a competitor configured to bind selectively to the second allelic form relative to the first allelic form and to block binding of the probe to the second allelic form. The first allelic form of the target may be amplified in the partitions. A signal may be detected from a label of the probe while the label is contained by the partitions. A number of partitions that are positive (or negative) for the at least one first allelic form may be determined based on the signal.

19 Claims, 5 Drawing Sheets

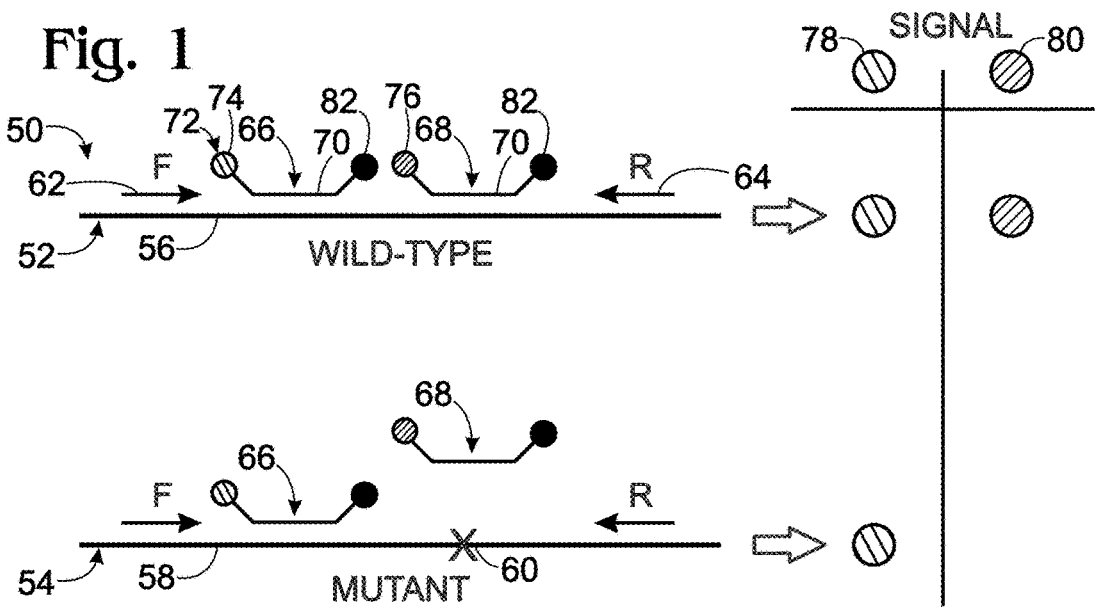
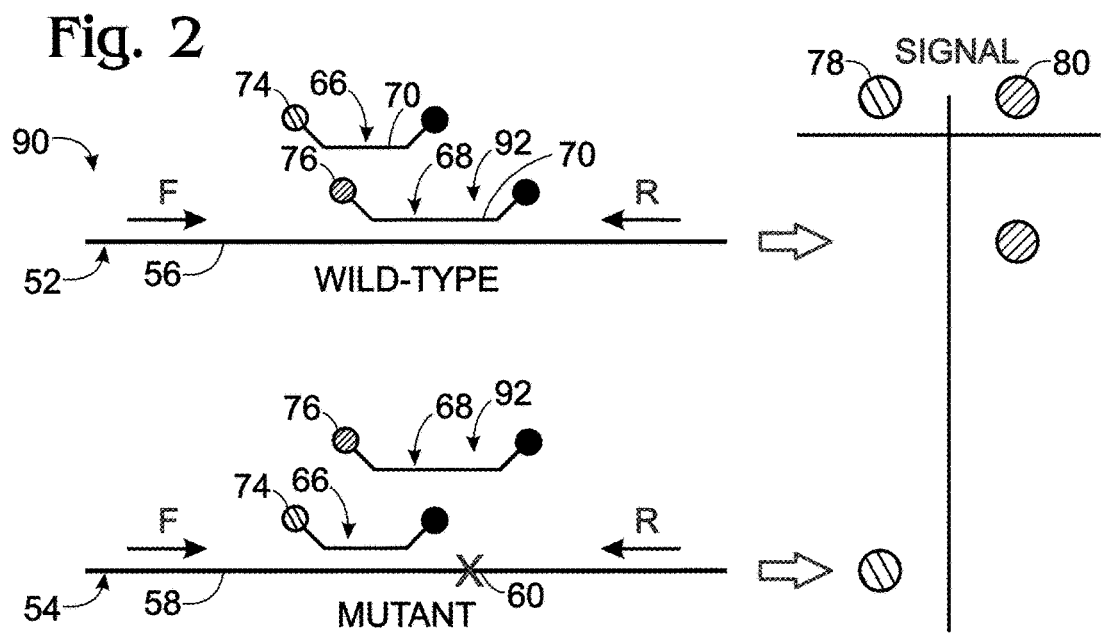

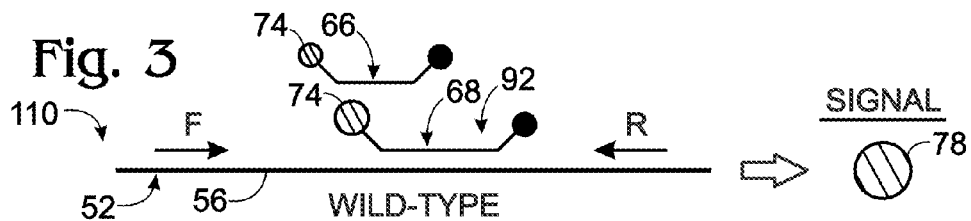
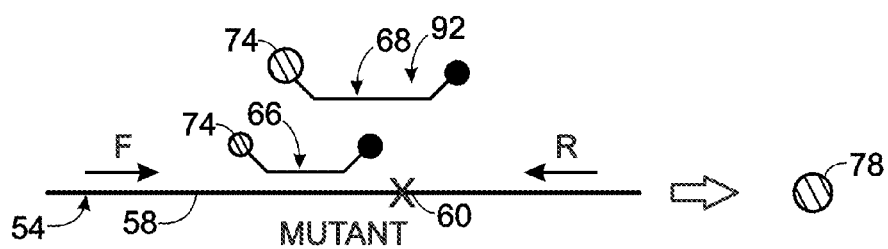
Fig. 3
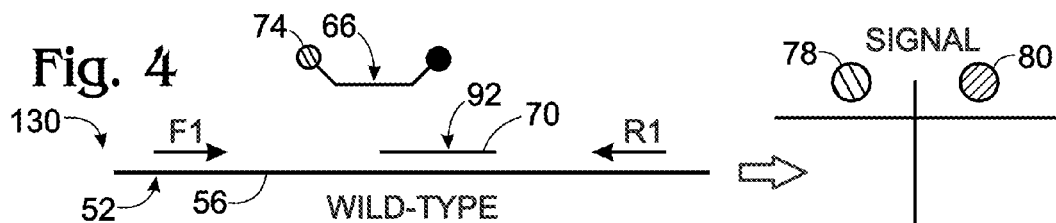
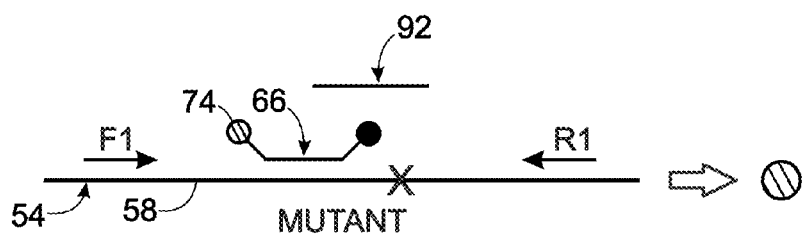
Fig. 4

142 — PREPARE MIXTURE CONTAINING A PROBE, A COMPETITOR, AND WILD-TYPE AND VARIANT FORMS OF A TARGET

144 — FORM PARTITIONS OF THE REACTION MIXTURE

146 — AMPLIFY THE TARGET WHILE THE COMPETITOR BLOCKS BINDING OF THE PROBE TO THE WILD-TYPE FORM

148 — DETECT A SIGNAL FROM A LABEL OF THE PROBE

150 — DETERMINE A NUMBER OF PARTITIONS CONTAINING A VARIANT FORM BASED ON THE SIGNAL

152 — CALCULATE A QUANTITY OF THE VARIANT FORM BASED ON THE NUMBER AND/OR THE SIGNAL

Fig. 6

WILD-TYPE
AAGTTAAAAATTCCCGTCGCTATCAAGGAATTAAGAGAAGCAACATCTCCGAAAGCCAACA (SEQ ID NO:1)

COMPETITOR
CGTCGCTATCAAGGAATTAAGAGAAGCA (SEQ ID NO:2)

PROBE
AATTCCCGTCGCTATCAA (SEQ ID NO:3)

DELETIONS

AAGTTAAAAATTCCCGTCGCTATCAA---------------AACATCTCCGAAAGCCAACA (SEQ ID NO:4)
AAGTTAAAAATTCCCGTCGCTATCAA-----(AAT)------ATCTCCGAAAGCCAACA (SEQ ID NO:5)
AAGTTAAAAATTCCCGTCGCTATCAAG-----------------ACATCTCCGAAAGCCAACA (SEQ ID NO:6)
AAGTTAAAAATTCCCGTCGCTATCAAGG-----(T)--------------TCCGAAAGCCAACA (SEQ ID NO:7)
AAGTTAAAAATTCCCGTCGCTATCAAGGA-------------------TCCGAAAGCCAACA (SEQ ID NO:8)
AAGTTAAAAATTCCCGTCGCTATCAAGGA-----(GC)----CAACATCTCCGAAAGCCAACA (SEQ ID NO:9)
AAGTTAAAAATTCCCGTCGCTATCAAGGA-----(GCA)---------ATCTCCGAAAGCCAACA (SEQ ID NO:10)
AAGTTAAAAATTCCCGTCGCTATCAAGGAA-----------------TCTCCGAAAGCCAACA (SEQ ID NO:11)
AAGTTAAAAATTCCCGTCGCTATCAAGGAA-------------------CCGAAAGCCAACA (SEQ ID NO:12)
AAGTTAAAAATTCCCGTCGCTATCAAGGAA----(C)----CAACATCTCCGAAAGCCAACA (SEQ ID NO:13)
AAGTTAAAAATTCCCGTCGCTATCAAGGAA----(C)------CATCTCCGAAAGCCAACA (SEQ ID NO:14)
AAGTTAAAAATTCCCGTCGCTATCAAGGAA---(CA)---------GAAAGCCAACA (SEQ ID NO:15)
AAGTTAAAAATTCCCGTCGCTATCAAGGAAT-------------------CCGAAAGCCAACA (SEQ ID NO:16)
AAGTTAAAAATTCCCGTCGCTATCAAGGAAT-------------CGAAAGCCAACA (SEQ ID NO:17)

AMPLIFICATION ASSAY WITH A PROBE COMPETITOR

CROSS-REFERENCE TO PRIORITY APPLICATION

This application is based upon and claims the benefit under 35 U.S.C. §119(e) of U.S. Provisional Patent Application Ser. No. 62/174,279, filed Jun. 11, 2015, which is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. Patent Application Publication No. 2013/0040841 A1, published Feb. 14, 2013; U.S. Patent Application Publication No. 2014/178889 A1, published Jun. 26, 2014; U.S. Patent Application Publication No. 2014/0221238 A1, published Aug. 7, 2014; and Joseph R. Lakowicz, PRINCIPLES OF FLUORESCENCE SPECTROSCOPY ($2^{nd}$ Ed. 1999).

INTRODUCTION

Digital assays generally rely on the ability to detect the presence or activity of individual copies of an analyte in a sample. In an exemplary digital assay, a sample is separated into a set of partitions, generally of equal volume. If copies of the analyte are distributed randomly among the partitions and the analyte is dilute enough, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, may be described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or, equivalently, the negative fraction then may be utilized to determine the concentration of the analyte in the partitions by Poisson statistics.

Amplification assays, such as those performed digitally, can be utilized to test for the presence of different alleles of a gene. For example, a mutant form of a target sequence can be distinguished from a corresponding wild-type form of the target sequence by the use of a "mutant" probe that binds specifically to the mutant form relative to the wild-type form. However, this approach generally requires use of a different mutant probe to detect the presence of each different mutant form, which can be expensive, time-consuming, and impractical. Also, if the mutant form is rare in a sample, the frequency of false positives for the mutant form may swamp out the frequency of true positives, making the assay unreliable for detecting the presence of a mutant sequence in a sample.

A new approach is needed to allow different variant sequences to be detected with the same probe and/or to increase the sensitivity for detecting rare mutant sequences in amplification assays.

SUMMARY

The present disclosure provides methods and compositions for detecting an allelic form of a target in amplification assays, which may be digital assays. In an exemplary method, partitions may be created that collectively contain at least one first allelic form (e.g., one or more variant forms) and a second allelic form (e.g., a wild-type form) of a target. Each partition may contain (i) a same probe capable of binding specifically to each of the first and second allelic forms of the target and (ii) a competitor configured to bind selectively to the second allelic form relative to the at least one first allelic form and to block binding of the probe to the second allelic form. The at least one first allelic form of the target may be amplified in the partitions. A signal may be detected from a label of the probe while the label is contained by the partitions. A number of partitions that are positive for the at least one first allelic form, or a number of partitions that are negative for the at least one first allelic form, may be determined based on the signal. A level of the at least one first allelic form may be calculated based on the number determined.

BRIEF DESCRIPTION OF THE DRAWINGS

FIG. 1 is a schematic illustration of a digital amplification assay for detecting variant and wild-type forms of a target, where the assay is performed without a competitor.

FIG. 2 is a schematic illustration of an exemplary amplification assay for detecting variant and wild-type forms of a target, where the assay is performed with a probe and a competitor attached to different labels, in accordance with aspects of the present disclosure.

FIG. 3 is a schematic illustration of another exemplary amplification assay for detecting variant and wild-type forms of a target, where the assay is performed with a probe and a competitor attached to different amounts of the same label, in accordance with aspects of the present disclosure.

FIG. 4 is a schematic illustration of still another exemplary amplification assay for detecting variant and wild type forms of a target, where the assay is performed with an unlabeled competitor and distinguishably labeled probes for detecting the variant form of the target and a reference that is not the target, in accordance with aspects of the present disclosure.

FIG. 5 is a flowchart of exemplary steps that may be performed in a digital amplification assay with a probe and a competitor, in accordance with aspects of the present disclosure.

FIG. 6 is an aligned set of sequences illustrating aspects of an exemplary embodiment of a digital amplification assay for detecting mutations in exon 19 of the human EGF receptor (EGFR), in accordance with aspects of the present disclosure.

DETAILED DESCRIPTION

Figure 7:
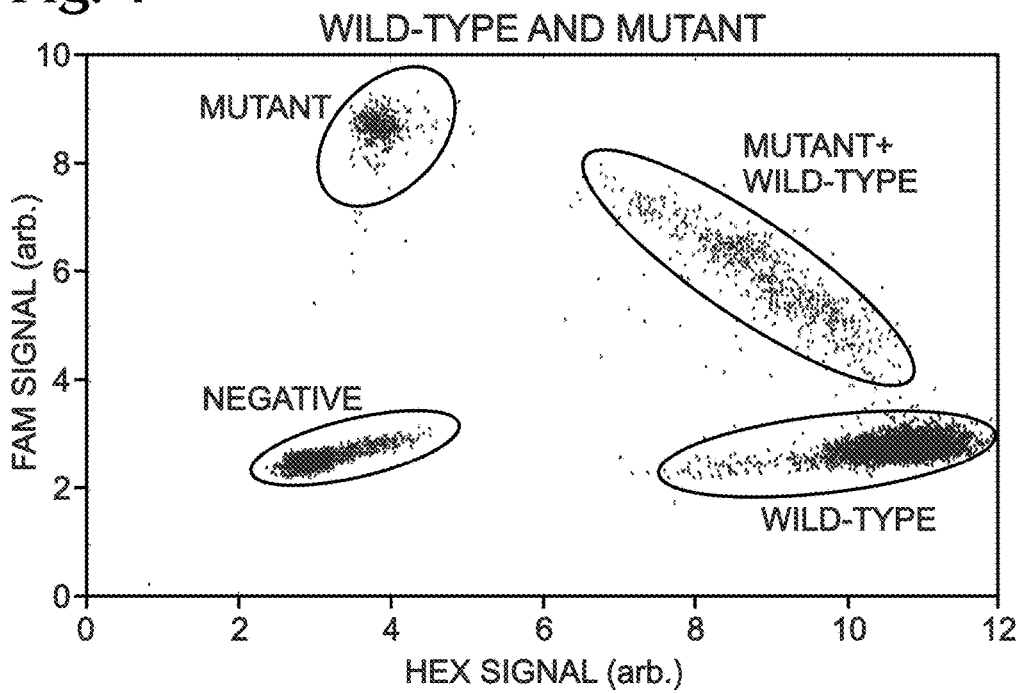
FIG. 7 is a graph of fluorescence signals detected from droplets that collectively contain mutant and wild-type forms of an exon 19 EGFR target after amplification of the target in the droplets in the presence of a FAM-labeled probe and a HEX-labeled competitor, generally according to the configuration of FIG. 2, in accordance with aspects of the present disclosure.

The present disclosure provides methods and compositions for detecting an allelic form of a target in amplification assays, which may be digital assays. In an exemplary method, partitions may be created that collectively contain at least one first allelic form (e.g., one or more variant forms) and a second allelic form (e.g., a wild-type form) of a target. Each partition may contain (i) a same probe capable of binding specifically to each of the first and second allelic forms of the target and (ii) a competitor configured to bind selectively to the second allelic form relative to the at least one first allelic form and to block binding of the probe to the second allelic form. The at least one first allelic form of the target may be amplified in the partitions. A signal may be detected from a label of the probe while the label is contained by the partitions. A number of partitions that are positive for the at least one first allelic form, or a number of partitions that are negative for the at least one first allelic form, may be determined based on the signal. A level of the at least one first allelic form may be calculated based on the number determined.

The methods and compositions of the present disclosure offer substantial advantages over other approaches for detecting allelic sequences, such as one or more variant forms and/or a wild-type form of a target. More specifically, the competitor, by blocking the binding of the probe to the wild-type form of the target, may reduce the level of the signal detected from a label of the probe in a given partition when only the wild-type form is present in the partition. This reduced signal may significantly diminish the fraction of partitions that are false positive for the variant form, to provide a higher sensitivity for variant detection. Also, the methods and compositions can detect any variant form of the target that destabilizes hybridization with the competitor, without destabilizing hybridization of the probe to the variant form. Accordingly, various deletions, insertions, and/or substitutions, which may occur at a localized mutation hotspot of a gene, each may be detectable with the same amplification assay, for each mutation that disrupts binding of the competitor, but not the probe, to the target.

Further aspects of the present disclosure are presented in the following sections: (I) exemplary assay configurations, (II) methods of quantifying a variant form of a target, (III) compositions, and (IV) examples.

I. Exemplary Assay Configurations

This section provides an overview of exemplary amplification assay configurations performed with or without a competitor and designed to detect and quantify an allelic form (such as at least one variant form (e.g., at least one mutant form)) of a target in a sample; see FIGS. 1-4.

Alleles are different forms of the same gene or other chromosomal region. A wild-type allele is the most prevalent form of a gene or other chromosomal region in a population of an organism (e.g., in a human population). A variant allele is a sequence variation of the wild-type allele. The variant allele may be present at any frequency in the population that is lower than the frequency of the wild-type allele. In some cases, the variant allele may be present at a frequency of less than 1%, in which case the variant allele may be described as a mutant allele. A target (also called a target sequence) may be any suitable region from a gene or other chromosomal region, and may have at least one first allelic form, originating from at least one first allele (e.g., one or more variant/mutant alleles of the gene), and a second allelic form, originating from a second allele (e.g., a wild-type allele of the gene). The target may have any suitable length, such as at least about 30, 40, 50, 75, or 100 nucleotides, among others.

FIGS. 1-4 show schematic representations of exemplary target, primer, probe, and competitor configurations for performing amplification assays, optionally digital assays performed in partitions, such as droplets. Each primer is positioned above and vertically aligned with an end region of the target at which each primer specifically binds by hybridization. Each probe is positioned above and vertically aligned with a region of the target (or a reference (see FIG. 4)) to which the probe can bind specifically by hybridization in the absence of the competitor, if any, for at least one form (e.g., the wild-type form) of the target. Each competitor is positioned above and vertically aligned with a region of the target to which the competitor can bind by hybridization for at least one form (e.g., the wild-type form) of the target. The vertical separation between each form of the target and each probe or competitor indicates whether or not binding is blocked by a competitor (for a probe) and/or whether or not binding is disrupted by a variation in the target sequence (e.g., by a mutation). In particular, each probe or competitor that is capable of binding specifically and is not blocked from binding to a given form of the target during and/or after amplification is horizontally aligned with the corresponding primers. In contrast, each probe or competitor that is incapable of binding specifically and/or is prevented from binding to a given form of the target during and/or after amplification is vertically offset from the primers and spaced farther from the given form of the target than when binding occurs.

FIG. 1 shows a schematic illustration of a digital amplification system 50 for detecting variant and wild-type forms of a target in a digital amplification assay. System 50 does not include a competitor and is included for comparison with other systems that utilize a competitor (e.g., see FIGS. 2-4). Any suitable aspects of system 50 may be present in the competitor-based systems shown in FIGS. 2-4.

The left portion of FIG. 1 shows a fragmentary view of a pair of polynucleotides or templates 52, 54 provided by a sample to be assayed. Templates 52, 54 originate from different alleles of the same gene or chromosomal region. The templates include different forms of the same target (also called a target sequence or a sequence), such as a wild-type form 56 and at least one variant form, such as at least one mutant form 58. Forms 56, 58 differ from one another at least one site of sequence variation 60 (indicated by an "X" in mutant form 58), which may be a polymorphism or a mutation (e.g., a deletion, an insertion, a substitution, or a combination thereof), among others. The sequences of wild-type form 56 and mutant form 58 may be identical to one another otherwise. A deletion, an insertion, or a substitution may remove (delete), add (insert), or replace (substitute) any suitable number of nucleotides, such as at least one, two, three, four, or five nucleotides, among others.

Forms 56, 58 of the target may be amplified in partitions with one or more primers contained in each of the partitions. For example, in the depicted embodiment, the same pair of primers (e.g., oligonucleotide primers), namely, a forward primer 62 ("F") and a reverse primer 64 ("R"), cooperate with one another to prime amplification of each form of the target. This amplification produces copies of each form of the target, also called amplified target or an amplicon for each target form. The primers may define the endpoints and thus the size of each form of the target and may bind to respective opposite ends of the target. In some embodiments, each form of the target may be amplified with the same primer, which acts as both a forward primer and a reverse primer. The same primer may prime amplification if, for example, both ends of each template 52, 54 are attached to the same adapter.

Amplification may be detected through the presence of one or more probes contained in the partitions. In the depicted embodiment, a pair of probes 66, 68 allow partitions containing mutant form 58 to be distinguished from those containing wild-type form 56.

Each probe 66, 68 may have a sequence-recognition portion 70 capable of binding specifically (e.g., hybridizing) to a region of at least one form of the target. Portion 70 may be provided by an oligonucleotide or an analogue thereof. Portion 70 of probe 66 is not form-specific and can hybridize with either form of the target. Portion 70 of probe 68 is wild-type specific and does not hybridize with the mutant form of the target.

Each probe 66, 68 may be a labeled probe that includes a label 72 to provide a detectable signal. Each label may be connected to sequence-recognition portion 70 (e.g., conjugated or connected noncovalently). The labels of the probes may be distinguishable from one another. For example, in the depicted embodiment, each label 72 is a photoluminophore 74, 76, such as a fluorophore, of different structure that emits a spectrally distinguishable signal 78 or 80. Each probe and/or sequence-recognition portion 70 also may be associated with (e.g., conjugated to) an energy transfer partner, such as a quencher 82 or a second photoluminophore. Quencher 82, through photoluminescence resonance energy transfer, may reduce the amount of photoluminescence detectable from each photoluminophore in a proximity-dependent manner. Accordingly, in some embodiments, cleavage (e.g., hydrolysis) of the probe catalyzed by a polymerase during amplification can separate the photoluminophore from the quencher to increase the signal. In other embodiments (e.g., with a molecular beacon probe), a conformational change of the probe produced by binding of the probe to amplified target causes the signal to increase. A second photoluminophore acting as an energy acceptor, if present in a probe, alternatively may emit the detectable signal and thus may be described as a label.

Signals 78, 80 detected after amplification of each target form are shown schematically in the right portion of FIG. 1. A partition originally containing at least one copy of wild-type form 56 provides binding sites for both probes 66, 68 in amplified target and thus is positive for signals 78, 80 detected from the label (here, photoluminophore 74 or 76) of each probe. In contrast, a partition originally containing at least one copy of mutant form 58 but no copies of wild-type form 56 provides a binding site only for probe 66 in the amplified target and thus is positive only for signal 78 detected from the label (photoluminophore 74) of probe 66.

The assay configuration shown in FIG. 1 may have certain drawbacks. First, wild-type and mutant forms 56, 58 are distinguished from one another based on the strength of only one of the signals, namely, signal 80. Accordingly, the rate of false positives for the mutant form can be high, with the wild-type form identified incorrectly as the mutant form whenever signal 80 from the wild-type form fluctuates below a threshold. As a result, in some cases, the quantity of the mutant form calculated may be an overestimate. Second, each partition that receives a copy of both target forms produces the same signal configuration as partitions that contain only the wild-type form, causing some copies of the mutant form to be missed. As a result, in some cases, the quantity of the mutant form calculated may be an underestimate. This underestimation can be avoided by forming the partitions at a higher dilution of the sample that minimizes co-occupancy of both target forms in the same individual partitions, but this higher dilution makes the assay less efficient to perform. Third, assay system 50 cannot be used effectively in a kinetic assay (e.g., real-time PCR) performed in a bulk phase, but instead requires a digital implementation to quantify the mutant form.

FIGS. 2-4 show competitor-based systems that overcome some or all of the drawbacks described above for system 50. Accordingly, each of the systems of FIGS. 2-4 can be used to perform a kinetic assay in a bulk phase, or a digital assay in partitions.

FIG. 2 shows a schematic illustration of another amplification system 90 for detecting wild-type and variant forms 56, 58 of a target. System 90 may have any suitable combination of the elements and features described above for system 50. For example, system 90 utilizes a probe 66 that is not form-specific and a wild-type-specific probe 68 as in system 50. (Probe 66 may be equally complementary to each form of the target (e.g., having the same melting temperature when hybridized with each form), and/or at least partially complementary or completely complementary to each form of the target.) However, wild-type-specific probe 68 is configured as a competitor 92 (also called a probe competitor) that competes with probe 66 for binding to at least partially overlapping regions of wild-type form 56. Competitor 92 is configured to outcompete probe 66 for binding to wild-type form 56, such that binding of probe 66 to the wild-type form is substantially reduced, which is described herein as being blocked. Probe 68/competitor 92 may be at least partially complementary or completely complementary to wild-type form 56 (or other allelic form).

Competitor 92 and probe 66 may form a binding hierarchy of probes, with competitor 92 (probe 68) dominant over probe 66. In some embodiments, one or more additional probes may be introduced, to form a binding hierarchy of three or more probes that bind to mutually overlapping regions of the wild-type form. With three or more probes, a larger region (e.g., a bigger mutation hotspot) may be analyzed in the assay and/or mutations may be more finely mapped.

Competitor 92 may bind more stably to wild-type form 56 than probe 66 binds to the wild-type form. In other words, competitor 92 may have a higher melting temperature when hybridized to the wild-type form than probe 66 hybridized to the wild-type form. Accordingly, sequence-recognition portion 70 (e.g., an oligonucleotide) of competitor 92 may be composed of more nucleotides than portion 70 of probe 66, may be more GC-rich, may have a different basic structure (e.g., a peptide nucleic acid), or a combination thereof, among others.

The respective binding sites for competitor 92 and probe 66 in wild-type form 56 may overlap by any suitable number of nucleotides, such as at least 3, 4, 5, 7, or 10 nucleotides, among others. In some embodiments, at least one-fourth, one-third, or one-half of the nucleotides of portion 70 of competitor 92 may bind to the same region of wild-type form 56 as probe 66 binds. In some embodiments, probe 66 has at least 5, 7, or 10 consecutive nucleotides arranged in a sequence that is also present in competitor 92.

Probe 66 and competitor 92 each may have any suitable melting temperature for hybridization with a form of the target. The melting temperature may be above or below an annealing temperature and/or an extension temperature at which target amplification may be performed, according to the type of probe being used and/or the temperature at which signal detection is performed. For example, a probe modified (e.g., degraded or extended) by the amplification process may have a melting temperature, for hybridization with a form of the target, that is above the annealing/extension temperature used for target amplification. In contrast, a probe (e.g., a molecular beacon probe) that is typically not modified by the amplification process may have a melting temperature, for hybridization with a form of the target, that is below the annealing/extension temperature used for target amplification.

The signals detected from assay system 90 are shown schematically at the right in FIG. 2 and should be compared to those of FIG. 1. Since binding of probe 66 and competitor 92 to each target form is mutually exclusive, amplification of each target form elevates the signal from only one of the two labels (photoluminophores 74 and 76). Signal 80 is elevated if wild-type form 56 is amplified. Signal 78 is elevated if mutant form 58 is amplified. If the assay is performed in partitions, a partition containing both forms 56 and 58 will have both signals elevated and will be distinguishable from a partition containing only wild-type form 56 or only mutant form 58. System 90 relative to system 50 may have a lower rate of false positives for the mutant form and may allow the assay to be performed with a higher concentration of the target and with fewer partitions for the same or more accurate results.

Signals 78, 80 may be analyzed to determine a first number of partitions containing (or not containing) the mutant form of the target and a second number of partitions containing (or not containing) the wild-type form of the target. A level of one or both forms of the target may be calculated based on the first number and/or the second number. In some embodiments, a relative copy number of the mutant form of the target may be calculated with respect to the wild-type form of the target based on the first and second numbers. For example, the relative copy number may be calculated as a ratio of the first and second numbers. In other cases, one of both numbers may be input values for an algorithm, such as a Poisson algorithm, that calculates a level of one or both targets, and then the relative copy number of the mutant form may be calculated as a ratio of the levels of the mutant and wild-type forms of the target.

FIG. 3 shows a schematic illustration of yet another amplification system 110 for detecting wild-type and variant forms 56, 58 of a target. System 110 may have any suitable combination of the elements and features described above for systems 50 and 90. System 110 is the same as system 90, except the same label, photoluminophore 74, is employed in probe 66 and competitor 92 (probe 68). However, probe 68 is configured to create a greater signal 78 than probe 66 when forms 56, 58 of the target are amplified in respective partitions. For example, a larger percentage of probe 68 molecules, relative to probe 66, may be labeled with photoluminophore. Alternatively, or in addition, probe 68 may be present in excess of probe 66, such that probe 66 is more limiting for signal generation. In any event, partitions containing only wild-type form 56 can be distinguished from those containing only mutant form 58 based on the strength of signal 80. Partitions containing both forms also may be distinguishable from those containing only one form.

Further aspects of multiplexed assays based on signal strength are described in the documents listed above under Cross-References, which are incorporated herein by reference, particularly U.S. Patent Application Publication No. 2013/0040841 A1, published Feb. 14, 2013; U.S. Patent Application Publication No. 2014/178889 A1, published Jun. 26, 2014; and U.S. Patent Application Publication No. 2014/0221238 A1, published Aug. 7, 2014.

FIG. 4 shows a schematic illustration of still another amplification system 130 for detecting wild-type and variant forms 56, 58 of a target. System 130 may have any suitable combination of the elements and features described above for systems 50, 90, and 110. However, system 130 may utilize an unlabeled competitor 92 to block binding of probe 66 to wild-type form 56. Competitor 92 has only sequence-recognition portion 70. Also, the system includes a template 132 that provides another target, namely, a reference target, which is called a reference 134. Wild-type and mutant forms 56, 58 of the target may be amplified with the same pair of forward and reverse primers, as described above, and which are identified as F1 and R1 in the depicted embodiment. Reference 134 may be amplified with a different pair of forward and reverse primers, F2 and R2. Amplification of reference 134 may be detected with a labeled probe 136, such as a probe including photoluminophore 76, while amplification of mutant form 58 is detected with probe 66 carrying photoluminophore 74, as described above for FIG. 2.

Signals 78, 80 detected as a result of amplification of each target are shown schematically on the right in FIG. 4. The presence and amplification of mutant form 58 is reported by signal 78, and of reference 134 by signal 80.

The presence and amplification of wild-type form 56 may not be reported by either signal. Accordingly, the assay can be performed with or without amplification of wild-type form 56. In some embodiments, competitor 92 may be configured to block amplification of wild-type form 56 selectively relative to mutant form 58. For example, competitor 92 may be resistant to degradation by the polymerase used for amplification, thereby allowing the competitor to impede extension of primer F1. The competitor thus may be a standard oligonucleotide that is degraded, or a degradation-resistant peptide nucleic acid or locked nucleic acid, among others.

Reference 134 and target forms 56, 58 may be provided by the same sample and may be present in copies of a same genome. The reference may have no overlap with target forms 56, 58, such that primers F1 and R1, probe 66, and competitor 92 do not bind specifically to the reference. The reference may be provided by a different (or the same) gene as the target, and may have a known or assumed copy number per genome of the sample. Accordingly, a relative copy number of mutant form 58 may be calculated with respect to reference 134, which allows the copy number of mutant form 58 per genome to be determined.

The same set of partitions (or the same bulk phase without partitioning) may be used to detect mutant form 58 and wild-type form 56 (or reference 134), as described above. Alternatively, portions of the same sample may be disposed in two different sets of partitions (or in two separate bulk phases). Mutant form 58 may be assayed with the one of the sets (or one of the bulk phases), and wild-type form 56 or reference 134 with the other set (or other bulk phase). Use of different sets of partitions (or different bulk phases)

allows the degree of dilution of the sample to be changed between the sets, to increase sensitivity for rare mutants.

II. Methods of Quantifying a Variant Form of a Target

This section describes exemplary methods of quantifying a variant form (or other allelic form) of a target in an amplification assay, which may be a digital assay performed in partitions, such as droplets, or in a bulk phase; see flowchart 140 of FIG. 5. The steps described in this section may be performed in any suitable order and combination, with any of the assay configurations, components, and features described elsewhere herein, such as in Sections I, III, and IV.

Reaction mixture preparation. A reaction mixture may be prepared containing at least one probe, a competitor (which may or may not also be a probe), and allelic forms of the same target, indicated at 142. The allelic forms of the target may include a wild-type form and at least one variant form (such as at least one mutant form) of the same target. The reaction mixture may be an amplification mixture configured to support amplification of each form of the target and thus may contain all of the reagents necessary for target amplification from templates provided by a sample that is present in the reaction mixture. The reaction mixture also may contain all of the reagents necessary for amplification of another target, namely, a reference (see FIG. 4). The reagents, which are described in more detail below, may, for example, include one or more primers, dNTPs and/or NTPs, a polymerase (e.g., an RNA polymerase or a DNA polymerase, either of which may or may not be heat stable), buffer, water, surfactant, and/or the like.

Polynucleotides in the reaction mixture serve as the initial templates for target/reference amplification and may have any suitable structure and characteristics. Each template may be at least predominantly single-stranded or at least predominantly double-stranded, among others, in the reaction mixture before target/reference amplification. Each template may, for example, be at least predominantly DNA (e.g., genomic DNA, mitochondrial DNA, or cDNA), at least predominantly RNA (e.g., genomic RNA, transcribed RNA, messenger RNA, tRNA, ribosomal RNA, etc.), a combination thereof (e.g., a DNA-RNA hybrid), or the like. Molecules of each template may be uniform in length (e.g., formed by restriction enzyme digestion or used as full-length), or may vary in size (e.g., formed by random fragmentation, such as shearing, digestion with a nonspecific nuclease, etc.). The templates may be provided by a nucleic acid sample that is a complex mixture of different nucleic acids (different polynucleotides), with templates for target/reference amplification being minor species. The nucleic acid sample may be composed substantially of genomic DNA, mitochondrial DNA, genomic RNA, total RNA, nuclear RNA, cytoplasmic RNA, messenger RNA, or any combination thereof, among others.

The reaction mixture also may include one or more primers that are complementary to and bind to the wild-type and variant templates and each form of the target (and, optionally, one or more primers that are complementary to and bind to the reference). The primers may be extendable by polymerase in the reaction mixture, when bound to a molecule of the template (and/or target/reference) to form a reaction product, such as at least part (e.g., one of the complementary strands) of a copy of amplified target/reference, also called amplified product. The primers may include a forward primer and a reverse primer for target amplification, which may be the same primer or distinct primers. The forward primer and the reverse primer may define the ends of each form of the target. A different pair of forward and reverse primers may define the ends of a reference that is amplified (see FIG. 4). In some examples, the target primers may have the same amount of complementarity to variant and wild-type templates and to each form of the target, such that the primers cannot distinguish between variant and wild-type templates and/or variant and wild-type forms of the target. Any of the primers disclosed herein may be oligonucleotides of any suitable length, such as at least 10, 15, or 20 nucleotides, among others.

Preparation of the reaction mixture may include or be described as preparation of a sample. Preparation of the sample may include any suitable manipulation of the sample, such as collection, dilution, concentration, purification, lyophilization, freezing, extraction, combination with one or more assay reagents, performance of at least one preliminary reaction to prepare the sample for one or more reactions in the assay, or any combination thereof, among others. Preparation of the sample may include rendering the sample competent for subsequent performance of one or more reactions, such as one or more enzyme catalyzed reactions and/or binding reactions.

In some embodiments, preparation of the sample may include combining the sample with reagents for amplification and one or more reporters (also called signaling agents) for reporting whether or not amplification occurred. Reagents for amplification may include any combination of one or more primers for synthesis of amplified target/reference, dNTPs and/or NTPs, at least one enzyme (e.g., a polymerase, a ligase, a reverse transcriptase, a restriction enzyme, or a combination thereof, each of which may or may not be heat-stable), and/or the like. Accordingly, preparation of the sample may render the sample (or partitions thereof) capable of amplification of each of the target forms and/or the reference, if present, in the sample (or a partition thereof). Reagents for reporting may include (a) a labeled probe that binds specifically to both a variant form and a wild-type form of the target, (b) a labeled probe that binds specifically to the wild-type form of the target relative to the variant form of the target, and/or (c) a labeled probe that binds specifically to the reference. Preparation of the sample for reporting may render the sample capable of reporting, or being analyzed for, whether or not amplification has occurred, for the variant form of the target, the wild-type form of the target, and/or the reference, and optionally the extent of any such amplification. Each probe may include a sequence-recognition portion (e.g., an oligonucleotide) for specific binding to the target/reference and a detectable label attached to the sequence-recognition portion. The label may, for example, be detectable optically, such as by detecting luminescence, absorption, scattering, polarization, energy transfer, or the like, involving the label. In exemplary embodiments, the label may be a photoluminophore (i.e., a photoluminescent moiety), such as a fluorophore.

The term "luminescence" means emission of light that cannot be attributed merely to the temperature of the emitting body. Exemplary forms of luminescence include photoluminescence, chemiluminescence, electroluminescence, or the like. A "luminophore" is any atom, associated group of atoms, moiety, molecule, or associated group of molecules capable of luminescence. Photoluminescence is any luminescence produced in response to irradiation with excitation light and includes fluorescence, phosphorescence, etc. Accordingly, a luminophore may be a photoluminophore, such as a fluorophore or a phosphor, among others.

The reporters may have any suitable structure and characteristics. Each reporter may be a probe that binds with specificity to a nucleotide sequence. The probe may include a nucleic acid. For example, the probe may include an oligonucleotide and a luminophore associated with the oligonucleotide (e.g., with the luminophore covalently attached to the oligonucleotide), to label the oligonucleotide. The probe also may or may not include or be otherwise associated with an energy transfer partner for the luminophore, such as a quencher, which may or may not be luminescent. The probe may be capable of binding specifically to the target (including amplified target) or the reference (including amplified reference). The probe may or may not also function as an amplification primer that forms part of a product (an amplicon) in the assay. Exemplary labeled probes include TaqMan® probes, Scorpion® probes/primers, Eclipse® probes, Amplifluor® probes, molecular beacon probes, Lux® primers, proximity-dependent pairs of hybridization probes that exhibit FRET when bound adjacent one another on an amplicon, QZyme® primers, or the like.

In some cases, at least one of the reporters may be a generic reporter, such as a fluorescent dye, that binds and labels nucleic acid relatively nonspecifically. For example, the fluorescent dye may have no covalent attachment to an oligonucleotide that confers substantial sequence binding specificity. The fluorescent dye may be a major groove binder, a minor groove binder, an intercalator, or an external binder, among others. The fluorescent dye may bind preferentially to double-stranded relative to single-stranded nucleic acid and/or may exhibit a greater change in a photoluminescent characteristic (e.g., intensity) when bound to double-stranded relative to single-stranded nucleic acid. Exemplary dyes that may be suitable include luminescent cyanines, phenanthridines, acridines, indoles, imidazoles, and the like, such as DAPI, Hoechst® 33258 dye, acridine orange, etc. Exemplary intercalating dyes that may be suitable include ethidium bromide, propidium iodide, EvaGreen® dye, SYBR® Green dye, SYBR® Gold dye, and 7-aminoactinomycin D (7-AAD), among others.

Formation of the reaction mixture may include forming a continuous phase or bulk phase containing all of the components necessary for target/reference amplification. Alternatively, or in addition, formation of the reaction mixture may include fusing partitions, such as droplets (see below) or fluid volumes in a well, to combine components of the reaction mixture.

The reaction mixture may be processed further as a bulk phase (interchangeably termed a continuous phase). Alternatively, the reaction mixture may be formed as a dispersed phase composed of a plurality of partitions that are isolated from one another by a solid phase (e.g., a wall of a container), a liquid phase (e.g., a carrier phase of an emulsion), a gas phase, or a combination thereof.

A target interchangeably may be termed an analyte, a target sequence, or, in some cases, a reference.

Partition creation. Partitions of the reaction mixture and/or of a sample providing target/reference templates may be formed (also termed "created"), indicated at 144. Stated another way, the reaction mixture and/or sample may be partitioned to form isolated fluid volumes, with each fluid volume containing a portion of the reaction mixture and/or sample.

The partitions when created may contain the at least one variant form of the target (the variant target form), the wild-type form of the target (the wild-type target form), and/or the reference at "partial occupancy," which means that a subset (one or more) of the partitions contains no copies of the target form/reference and the rest of partitions contain at least one copy of the target form/reference. For example, another subset (one or more) of the partitions may contain a single copy (only one copy) of the target form/reference, and, optionally, yet another subset (one or more) of the partitions (e.g., the rest of the partitions) may contain two or more copies of the target form/reference. The term "partial occupancy" permits but does not require a dilution of the sample/reaction mixture providing the target form/reference, and is not restricted to the case where there is no more than one copy of the target form/reference in any partition. Accordingly, partitions containing the target form/reference at partial occupancy may, for example, contain an average of more than, or less than, about one copy, two copies, or three copies, among others, of the target form/reference per partition when the partitions are formed. Copies of the target form/reference (and templates therefor) may have a random distribution among the partitions, which may be described as a Poisson distribution.

Partition formation may involve distributing any suitable portion including up to all of the sample/reaction mixture to the partitions. Each partition is spatially isolated from every other partition, and may be and/or include a fluid volume that is isolated from fluid volumes of other partitions. The partitions may be isolated from one another by a fluid/liquid phase, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with at least one droplet generator having an orifice and/or a channel intersection at which droplets are created, by agitation of the sample/reaction mixture (e.g., shaking, stirring, sonication, etc.), and/or the like. Accordingly, the partitions may be formed serially, in parallel, or in batch. The partitions may have any suitable volume or volumes. The partitions may have the same volume or may have different volumes. Exemplary partitions having the same volume are monodisperse droplets. Exemplary volumes for the partitions include an average volume of less than about 100, 10 or 1 µL, less than about 100, 10, or 1 nL, or less than about 100, 10, or 1 pL, among others.

Partitions competent for amplification of each target form and/or a reference may be formed directly from a bulk phase containing copies of the target and/or reference, or may be formed in multiple steps. In some cases, the step of forming partitions may include dividing a bulk phase into isolated fluid volumes (such as droplets) containing the at least one mutant target form and/or the wild-type target form at partial occupancy. The fluid volumes may be the partitions themselves or may contribute to the partitions. For example, the fluid volumes may be a first set of fluid volumes, and the step of forming partitions may include combining individual fluid volumes of the first set with individual fluid volumes of a second set. The second set may include one or more reagents for amplification of one or more of the targets, such as at least one primer for amplification of at least one of the targets, a probe, or the like. The step of combining may include fusing fluid volumes of the first set individually with fluid volumes of the second set, such as fusing droplets containing the template with droplets containing primers for amplification of one or more targets from the template.

Target amplification. The variant form of the target may be amplified while the competitor blocks binding of the probe to the wild-type form of the target, indicated at 146. The variant form amplified may be a plurality of different variant forms that are not distinguished from one another by the assay. The step of amplifying also may amplify the wild-type form and/or a reference. In some embodiments, amplification of the wild-type form may be blocked specifically by the competitor (see FIG. 3), such as when the competitor is designed to be resistant to degradation by the polymerase.

Amplification may be performed in partitions (a dispersed phase) or in a continuous phase, such as in the reaction mixture without forming partitions. If performed in partitions, amplification of each target form and/or the reference may occur in only a subset of the partitions, such as less than about three-fourths, one-half, one-fourth, or one-tenth of the partitions, among others. Amplification of each target form and/or the reference may occur only in partitions containing at least one copy of the target form/reference (i.e., containing at least one copy of a template corresponding to the target form/reference).

Amplification may or may not be performed isothermally. In some cases, amplification in the partitions may be encouraged by thermal cycling, namely, subjecting the partitions to multiple cycles of heating and cooling. The partitions may be incubated at a denaturation temperature (e.g., greater than about 90 degrees Celsius), an annealing temperature (e.g., about 50-75 degrees Celsius), and/or an extension temperature (e.g., about 60 to 80 degrees Celsius), for one or a plurality of cycles. In some examples, the partitions may be thermally cycled to promote a polymerase chain reaction and/or ligase chain reaction. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

Signal detection. A signal may be detected from a label of the probe, indicated at 148. The signal may be detected from a bulk phase, if partitions have not been formed. For example, the signal may be detected in a kinetic assay (in real time) over the course of multiple cycles to determine how many cycles are needed to amplify the mutant form to a threshold (e.g., half-maximal). With the use of partitions, the signal may be detected from intact partitions, while the label is contained by the partitions, optionally in an endpoint assay. More generally, a signal may be detected from at least one label of each reporter/probe of the assay to collect data representing amplification of one or more target forms and/or the reference in a bulk phase or individual partitions.

The signal may represent any detected form of energy, such as electromagnetic, electric, magnetic, or the like. In exemplary embodiments, the signal represents a property of detected visible, ultraviolet, and/or infrared light.

Light dependent at least in part on a luminophore of a probe(s) may be detected. The light may be emitted by the luminophore directly or may be emitted by an energy transfer partner of the luminophore, among others. Detection of light may be described as collection of amplification data. The data may be collected by detecting light emitted from individual intact partitions or from a bulk phase reaction mixture. The light may be emitted in response to irradiation of the partitions or reaction mixture with excitation light for the luminophore(s) or an energy transfer partner thereof. The data may be collected for emission of light from the partitions or reaction mixture in one spectral region (one optical channel), a pair of different spectral regions (two optical channels) (e.g., one for each target/probe), or the like. The different spectral regions are defined by different wavelengths and/or wavebands relative to one another.

An optical channel may represent a particular detection regime with which emitted light is generated and detected. The detection regime may be characterized by a wavelength/waveband (i.e., a wavelength regime) for detection of emitted light. If pulsed excitation light is used in the detection regime to induce light emission, the detection regime may be characterized by a wavelength or waveband for illumination with excitation light and/or a time interval during which light emission is detected with respect to each light pulse. Accordingly, optical channels that are different from each other may differ with respect to the wavelength/waveband of excitation light, with respect to the wavelength/waveband of emitted light that is detected, and/or with respect to the time interval during which emitted light is detected relative to each pulse of excitation light, among others.

Data collection may include detecting one or more signals from individual partitions or the reaction mixture. The signals may represent a property of light, such as the intensity, polarization, or lifetime of the light, among others. The signals optionally may include data collected in two or more different optical channels (e.g., in different wavelengths/wavelength ranges (wavebands) and/or color regimes) from probes/reporters for the same and/or different targets). The light detected from each probe/reporter may be light emitted by a luminophore (e.g., a fluorophore). The light detected in a given optical channel may be detected such that light from different probes/reporters is summed or accumulated without attribution to a particular probe/reporter. Thus, the signal for a given channel may be a composite signal that represents two, three, four, or more targets or target forms. In other cases, the signals for the targets and/or target forms may be detected in different optical channels.

The signal(s) may represent detected light emitted from one or more probes/reporters in the partitions. The one or more probes/reporters may report whether at least one of two or more particular amplification reactions represented by the signal has occurred in a partition and thus whether at least one copy of at least one of two or more particular targets or target forms corresponding to the two or more particular amplification reactions is present in the partition. The level or amplitude of the signal corresponding to the reporters may be analyzed to determine whether or not at least one of the particular amplification reactions has occurred and at least one copy of one of the particular targets or target forms is present. The level or amplitude of the signal may vary among the partitions according to whether at least one of the particular amplification reactions occurred or did not occur and at least one of the particular targets or target forms is present or absent in each partition. For example, a partition testing positive for a particular target or target form only may produce a signal value that is above a given threshold and/or within a given range. Partitions may be analyzed and signals detected at any suitable time(s). Exemplary times include at the end of a reaction phase of the assay (an endpoint assay), when reactions have run to completion and the data no longer are changing, or at some earlier time, as long as the data are sufficiently and reliably separated.

Data may be collected from a plurality of the partitions (i.e., only a subset or all of the partitions) under any suitable conditions. All of the data may be collected at about the same temperature from the plurality of partitions, such as at a temperature that is below a melting temperature of each amplicon, and/or below about 50 degrees Celsius, among others.

Obtaining partition signal values. The signal detected from each label or in each optical channel (e.g., at each wavelength or wavelength region) may be processed to obtain a signal value for each partition. For example, the signal may be parsed to identify a signal portion corresponding to each partition. Then, a signal value for the partition may be obtained from the signal portion, such as by integrating over the signal portion, taking a maximum or average value of the signal over the signal portion, or the like. In any event, each partition may be assigned a signal value for each label and/or optical channel. The size of the signal value(s) associated with each partition is used to determine whether the partition contains the variant form of the target, and, optionally, whether the partition contains the wild-type form and/or the reference.

Enumerate partitions. A number of partitions containing the at least one variant form of the target may be determined based on the signal detected from the label, indicated at 150. A number of partitions containing the wild-type form of the target and/or a number of partitions containing the reference also may be determined, based on one or more signals detected from the same label and/or at least one other label (e.g., see FIGS. 2-4).

Each number of partitions may be determined based on the partition signal values obtained from one or more signals. For example, one or more signal values for each partition may be compared with at least one threshold (and/or range) to determine whether the partition contains a given target form or the reference.

The number of partitions for each target form and/or the reference may be determined from the same set of partitions. Alternatively, a different set of partitions may be utilized to determine the number of partitions containing the wild-type form of the target and/or the reference. For example, a lower dilution of a sample in one set of partitions may provide more sensitive detection of a rare mutant form, while a higher dilution of the same sample in another set of partitions may provide a more accurate determination of the level of a wild-type form/reference.

Partition populations (interchangeably termed clusters or bands) that test negative or positive for one or more target forms and/or targets may be identified based on their signal values. Identification may be performed by a data processor using an algorithm (e.g., an algorithm that identifies patterns (e.g., partition clusters) in the data), by a user, or a combination thereof. In some cases, a data processor may produce and output (e.g., display) a plot of the signal values (e.g., a graph, a 2-D scatter plot, a histogram, or the like). The user then may define the boundary of each population based on the plot(s), e.g., through a graphical user interface to define population boundaries, and/or by inputting values (e.g., representing thresholds/ranges for the signals values) to define a boundary for each population. Each population boundary may be defined by one or more ranges of values, a geometrical shape that surrounds the population (e.g., a polygon, ellipse, etc.), or the like. Algorithms may be used to define the population boundaries with or without user input.

Identification of partition populations may include assigning each partition to one of a plurality of predefined bins each corresponding to a distinct partition population having a distinct target form/target content. The predefined bins may represent all combinations of negatives and positives for the target forms/targets.

Calculation of a quantity of the variant form. A quantity of the at least one variant form may be calculated, indicated at 152. Calculation may be based on the number of partitions determined to contain the variant form, if the assay is performed with partitions, or based on the signal detected from the label of the probe, if the assay is performed in a bulk phase.

The quantity may be an absolute or relative level of the variant form. The absolute level may, for example, be a number of molecules/copies of the variant form, or a concentration of the variant form (e.g., per partition or per unit volume), among others. The relative level may, for example, be a relative copy number of the variant form with respect to the wild-type form or with respect to a reference target, among others. The relative level alternatively may be a relative quantity of the variant form expressed per genome, per mass of nucleic acid (e.g., per mass of genomic DNA), or the like.

A relative copy number may be calculated, in some cases, by directly comparing (e.g., taking a ratio of) the number of partitions containing the variant form and the number of partitions containing the wild-type form or a reference target. In other cases, a number of molecules or copies (or an average number of molecules/copies per partition) of each target form and/or the reference contained by the partitions may be calculated from the number of partitions containing the target form/reference, as described in more detail below. Then, the numbers of molecules or copies (or the average numbers per partition) may be compared (e.g., as a ratio) to calculate a relative copy number.

The level may represent the level of the target or target form that was present before amplification. Determination of levels may (or may not) be based on each target or target form having a Poisson distribution among the partitions. Each level may, for example, be a value representing the total number of partitions positive (or negative) for the target or target form, or a concentration value, such as a value representing the average number of copies of the target or target form per partition or unit volume, among others. The partition data further may be used (e.g., directly and/or as concentration data) to estimate copy number (CN) and copy number variation (CNV), or any other property of the sample, using any suitable algorithms.

A level (e.g., concentration) of each target (or target form) may be determined with Poisson statistics. The concentration may be expressed with respect to the partitions (or reaction mixture) and/or with respect to a sample providing the target. The concentration of the target in the partitions may be calculated from the fraction of positive partitions (or, equivalently, the fraction of negative partitions) by assuming that copies of the target (before amplification) have a Poisson distribution among the partitions. With this assumption, the fraction f(k) of partitions having k copies of the template is given by the following equation:

$$f(k) = \frac{\lambda^k}{k!} e^{-\lambda} \qquad (1)$$

Here, $\lambda$ is the concentration of the target in the partitions, expressed as the average number of target copies per partition (before amplification). Simplified Poisson equations (also called algorithms) may be derived from the more general equation above and may be used to determine target concentration from the fraction of positive partitions. An exemplary Poisson equation that may be used is as follows:

$$\lambda = -\ln\left(1 - \frac{N_+}{N_{tot}}\right) \quad (2)$$

where $N_+$ is the number of partitions (i.e., the partition count) positive for a given target, and where $N_{tot}$ is the total number of partitions that are positive or negative for the target. $N_{tot}$ is equal to a sum of (a) $N_+$ for the target and (b) the number of partitions negative for the target, or $N_-$. $N_+/N_{tot}$ (or $N_+/(N_++N_-)$) is equal to $f_+$, which is the fraction of partitions positive for the template (i.e., $f_+=f(1)+f(2)+f(3)+\ldots$) (see Equation 1), and which is a measured estimate of the probability of a partition having at least one copy of the template. Another exemplary Poisson equation that may be used is as follows:

$$\lambda = -\ln\left(\frac{N_-}{N_{tot}}\right) \quad (3)$$

where $N_-$ and $N_{tot}$ are as defined above. $N_-/N_{tot}$ is equal to $f_-$, the fraction of negative partitions (or $1-f_+$), and is a measured estimate of the probability of a partition having no copies of the target, and $\lambda$ is the target concentration as described above.

Equations 2 and 3 above can be rearranged to produce the following:

$$\lambda = \ln(N_{tot}) - \ln(N_{tot}-N_+) \quad (4)$$

$$\lambda = \ln(N_{tot}) - \ln(N_-) \quad (5)$$

The concentration of each target in an assay can, for example, be determined with any of Equations 2 to 5, using values (i.e., partition counts) obtained for $N_{tot}$ and $N_-$ or, equivalently, $N_+$, for each target. In some cases, the value used for $N_{tot}$ (the total partition count) may be the same for each target. In other cases, the value used for $N_{tot}$ may vary, such as if some of the populations are excluded from the total count due to population overlap. In some embodiments, $N_{tot}$ may be equivalent to a combination of all populations, namely, a sum of the partition counts for all populations identified.

In some embodiments, an estimate of the level of a target (and/or the template) may be obtained directly from the positive fraction, without use of Poisson statistics. In particular, the positive fraction and the concentration (copies per partition) converge as the concentration decreases. For example, with a positive fraction of 0.1, the concentration is determined with Equation 2 to be about 0.105, a difference of only 5%; with a positive fraction of 0.01, the concentration is determined to be about 0.01005, a ten-fold smaller difference of only 0.5%. However, the use of Poisson statistics can provide a more accurate estimate of concentration, particularly with a relatively higher positive fraction, because Poisson statistics takes into account the occurrence of multiple copies of the same target (or target form)/template in the same partitions.

Further aspects of sample preparation, partition formation, amplification, signal detection, signal processing, obtaining partition counts, and calculating levels/quantities, among others, that may be suitable for the system of the present disclosure are described elsewhere in the present disclosure, and in the references identified in the Cross-References, which are incorporated herein by reference.

III. Compositions

This section provides exemplary compositions of the present disclosure. Each composition may or may not contain all the reagents necessary for amplification of a nucleic acid target, such as by PCR.

The composition may include at least one volume of fluid or a plurality of isolated partitions collectively containing a wild-type form and at least one variant form of a target. The variant form of the target (and, optionally, the wild-type form) may be present at partial occupancy in the partitions. The volume of fluid and/or each partition may contain a probe capable of specifically binding to each form of the target. The probe may be labeled, such as with a photoluminophore and/or a quencher. The volume of fluid and/or each partition also may contain a competitor configured to bind specifically to the wild-type form relative to the variant form and to block binding of the probe to the wild-type form. The competitor also may be a labeled probe.

The volume of fluid and/or each partition further may contain reagents to amplify the variant form of the target. The reagents may include at least one or a same pair of primers to amplify each form of the target. The reagents also may include a polymerase, such as a heat-stable polymerase, and dNTPs, among others.

The partitions may be isolated from one another by a continuous phase, such as liquid phase that is immiscible with each partition. The liquid phase may include an oil and, optionally, a surfactant.

IV. Examples

The following examples describe selected aspects and embodiments of amplification assays for variant detection performed with a competitor. These aspects and embodiments are intended for illustration and should not limit the entire scope of the present disclosure.

Example 1

Digital Assay of Exon 19 Mutations of EGFR

Figure 8:
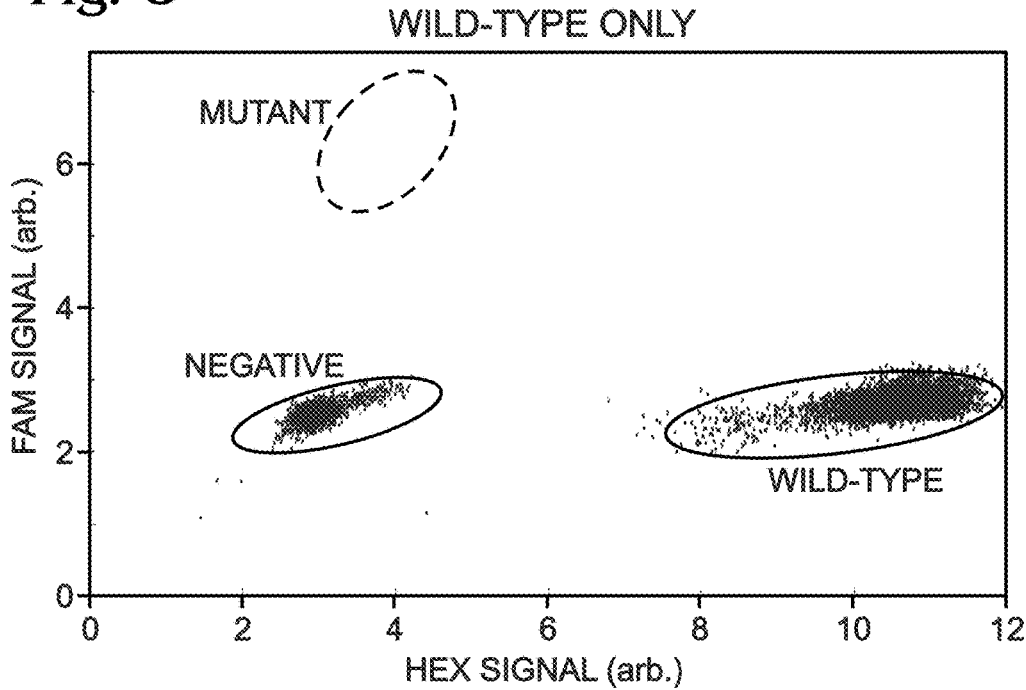
FIG. 8 is a graph of fluorescence signals detected from droplets as in FIG. 7, except with the droplets containing only the wild-type form of the target, in accordance with aspects of the present disclosure.

This example describes exemplary digital amplification assays for detecting the presence of mutations in exon 19 of the epidermal growth factor receptor (EGFR); see FIGS. 6-8.

FIG. 6 shows a vertically aligned set of sequences (SEQ ID NOS:1-17) illustrating aspects of an exemplary embodiment of an amplification assay for detecting mutations in exon 19 of human EGFR. The sequence at the top (SEQ ID NO:1) is a 60-nucleotide sequence present in exon 19 of human wild-type EGFR and contains a hotspot for deletions.

The nucleotide sequences of a competitor (SEQ ID NO:2) and a probe (SEQ ID NO:3) for the assay are listed under the wild-type sequence. The competitor and probe may be labeled with different fluorophores. For example, for the data presented in this Example, the competitor is labeled at its 5' terminus with a HEX fluorescent dye, and the probe is labeled at the 5' terminus with a FAM fluorescent dye, with each dye conjugated to the 5' terminal nucleotide of the corresponding oligonucleotide. Each of the competitor and probe also is conjugated to Iowa Black® fluorescence quencher at the 3' terminus.

The competitor is 28 nucleotides in length (12/28 G or C), while the probe is only 18 nucleotides in length (8/18 G or C). Accordingly, the competitor has a significantly higher melting temperature than the probe when each is bound to the wild-type sequence. The probe and the competitor have an overlap of 12 nucleotides, which is less than one-half the length of the competitor and greater than one-half the length of the probe.

Exon 19 of the EGFR is a hotspot for mutations that promote carcinogenesis. Fourteen exon 19 deletion mutations that have been identified are listed in FIG. 6 as SEQ ID NOS:4-17. Nucleotides deleted relative to wild-type are identified with dashes, and inserted nucleotides are enclosed by parentheses. Each deletion removes ten to nineteen nucleotides of the wild-type sequence. The competitor overlaps the hotspot significantly; a minimum of ten nucleotides of the wild-type sequence complementary to the competitor sequence is removed from each of the deletions, which effectively eliminates binding of the competitor to each mutant relative to wild-type. Accordingly, each of the deletions shown may be detected in an amplification assay with the same probe and competitor exemplified here. Smaller deletions or even point mutants also may be detected, in some cases, but deletions of the size shown here are more efficiently and reliably detectable with the assay configuration exemplified here.

Amplification of a 92-nucleotide EGFR sequence (SEQ ID NO:18) was performed by PCR in droplets with Taq DNA Polymerase. A forward primer (SEQ ID NO:19) and a reverse primer (SEQ ID NO:20) of 19 and 20 nucleotides in length, respectively, primed amplification. Fluorescence of the droplets was detected from the FAM fluorescent dye and the VIC fluorescent dye at different wavelengths for a stream of droplets flowing past a fluorescence detector, to provide a FAM dye signal and a VIC dye signal measured over time. The FAM and VIC signal values (in arbitrary units (arb.)) obtained for individual droplets were graphed to produce the scatter plots of FIGS. 7 and 8, where the two signal values (FAM and VIC) for each droplet are represented by the position of a dot in the plot.

FIG. 7 shows a plot of droplet signal values detected from droplets containing mutant and wild-type forms of an exon 19 EGFR target, after amplification of the target in the droplets. The mutant form is 149_EGFR_L747_A750>P (SEQ ID NO:9). Clusters of droplets containing neither form ("negative"), only the mutant form ("mutant"), only the wild-type form ("wild-type"), and both forms are identified in the plot.

FIG. 8 shows a plot of droplet signal values detected from droplets as in FIG. 7, but with the droplets containing only the wild-type form of the target. No false-positive droplets are detectable within the mutant region identified by a dashed ellipse (compare FIGS. 7 and 8). The rate of false-positives for the mutant form was measured to be only about 1 in $10^5$ droplets, which allows rare mutants to be detected in a sample.

Example 2

Selected Embodiments

This example describes selected embodiments of the present disclosure presented as a series of index paragraphs.

Paragraph A1. A method of detecting an allelic form of a target, the method comprising: (a) creating partitions collectively containing at least one first allelic form and a second allelic form of a target, each partition containing (i) a same probe capable of binding specifically to each of the first and second allelic forms of the target and (ii) a competitor configured to bind selectively to the second allelic form relative to the at least one first allelic form and to block binding of the probe to the second allelic form; (b) amplifying the at least one first allelic form of the target in the partitions; (c) detecting a signal from a label of the probe while the label is contained by the partitions; and (d) determining a number of partitions that are positive for the at least one first allelic form, or a number of partitions that are negative for the at least one first allelic form, based on the signal.

Paragraph A2. The method of paragraph A1, wherein the probe and the competitor are configured to hybridize to partially overlapping regions of the second allelic form of the target.

Paragraph A3. The method of paragraph A1 or paragraph A2, wherein the at least one first allelic form includes a first allelic form having a deletion of two or more nucleotides relative to the second allelic form within a region that is complementary to the competitor.

Paragraph A4. The method of any of paragraphs A1 to A3, further comprising a step of calculating a level of the at least one first allelic form based on the number determined.

Paragraph A5. The method of paragraph A4, wherein the step of calculating includes a step of calculating a relative copy number of the at least one first allelic form.

Paragraph A6. The method of paragraph A5, wherein the relative copy number is calculated relative to the second allelic form or a reference that is not a form of the target.

Paragraph A7. The method of paragraph A5, wherein the partitions are a first set of partitions created from a first mixture containing a portion of a sample that includes each allelic form of the target, further comprising a step of creating a second set of partitions from a second mixture containing a portion of the sample, wherein the number is determined from the first set, and wherein the step of calculating is based on the number determined from the first set, and on a number of partitions of the second set that are positive for the second allelic form or a reference, or a number of partitions of the second set that are negative for the second allelic form or a reference.

Paragraph A8. The method of paragraph A7, wherein the at least one first allelic form is one more variant forms of the target, wherein the second allelic form is a wild-type form of the target, and wherein the sample is more dilute in the second set of partitions than in the first set of partitions.

Paragraph A9. The method of any of paragraphs A1 to A6, the probe being a first probe, wherein the competitor is a second probe, wherein the step of detecting a signal includes a step of detecting one or more signals from a label of the first probe and a label of the second probe, further comprising a step of determining a number of partitions that are positive for the second allelic form, or a number of partitions that are negative for the second allelic form based on at least one of the one or more signals.

Paragraph A10. The method of paragraph A9, further comprising a step of calculating a level of the second allelic form based on the number determined for the second allelic form.

Paragraph A11. The method of paragraph A10, wherein the step of calculating includes a step of determining a copy number of the at least one first allelic form relative to the second allelic form based on both numbers determined.

Paragraph A12. The method of paragraph A11, wherein the step of determining a copy number of the at least one first allelic form includes a step of calculating a ratio of the number of partitions positive for the at least one first allelic form and the number of partitions positive for the second allelic form.

Paragraph A13. The method of paragraph A10, wherein the step of determining a relative copy number of the at least one first allelic form includes a step of calculating a level of the at least one first allelic form and a level of the second allelic form based on a Poisson algorithm, and a step of calculating a ratio of the level of the at least one first allelic form and the level of the second allelic form.

Paragraph A14. The method of any of paragraphs A9 to A13, wherein the first probe and the second probe are each labeled with a different photoluminophore relative to one another.

Paragraph A15. The method of any of paragraphs A1 to A14, wherein a melting temperature of the competitor hybridized with the second allelic form of the target is greater than a melting temperature of the probe hybridized with the second allelic form of the target.

Paragraph A16. The method of any of paragraphs A1 to A15, wherein each partition when created contains more of the competitor than the probe on a molar basis.

Paragraph A17. The method of any of paragraphs A1 to A6 and A9 to A16, wherein each allelic of the target is provided by a sample including a reference that is not the target, wherein the step of amplifying includes a step of amplifying the reference, further comprising a step of calculating a relative copy number of the at least one first allelic form with respect to the reference.

Paragraph A18. The method of any of paragraphs A1 to A17, wherein the step of amplifying includes a step of amplifying each allelic of the target with the same pair of primers.

Paragraph A19. The method of any of paragraphs A1 to A18, wherein the partitions are droplets.

Paragraph A20. The method of any of paragraphs A1 to A19, wherein the step of amplifying degrades at least a molar fraction of the probe.

Paragraph A21. The method of any of paragraphs A1 to A20, wherein the step of amplifying degrades at least a molar fraction of the competitor.

Paragraph A22. The method of paragraph A21, wherein a molar fraction of the competitor remains intact when the step of amplifying is completed.

Paragraph A23. The method of any of paragraphs A1 to A22, wherein the step of amplifying is catalyzed by a polymerase that catalyzes degradation of at least a molar fraction of the probe during the step of amplifying, and wherein the competitor is resistant to degradation catalyzed by the polymerase, such that amplification of the second allelic form of the target is blocked by the competitor.

Paragraph A24. The method of any of paragraphs A1 to A23, wherein the probe is capable of binding specifically to each of the first and second allelic forms of the target below a melting temperature (interchangeably called a hybridization temperature).

Paragraph A25. The method of paragraph A24, wherein the step of amplifying is performed at least in part below the melting temperature.

Paragraph A26. The method of paragraph A24 or A25, wherein the step of amplifying includes a step of annealing at least one primer to the first and second allelic forms of the target and a step of extending the at least one primer after the step of annealing, and wherein the step of annealing is performed below the melting temperature.

Paragraph A27. The method of any of paragraphs A24 to A26, wherein the step of amplifying includes a step of extending at least one primer that is hybridized to the first and second allelic forms of the target, and wherein the step of extending is performed below the melting temperature.

Paragraph A28. The method of any of paragraphs A24 to A27, wherein the step of detecting is performed with the partitions below the melting temperature.

Paragraph A29. The method of paragraph A24, wherein the step of amplifying is performed entirely above the melting temperature.

Paragraph A30. The method of paragraph A29, wherein the step of amplifying includes a step of thermocycling the partitions through multiple thermal cycles, and wherein the partitions are above the melting temperature throughout each of the thermal cycles.

Paragraph B1. A method of detecting an allelic form of a target, the method comprising: (a) preparing a mixture including (i) at least one first allelic form of a target and a second allelic form of the target, (ii) a same probe capable of binding specifically to each of the first and second allelic forms of the target, and (iii) a competitor configured to bind selectively to the second allelic form relative to the at least one first allelic form and to block binding of the probe to the second allelic form; (b) dividing at least a portion of the mixture into partitions, wherein each partition of only a subset of the partitions contains the at least one first allelic form of the target; (c) amplifying the at least one first allelic form of the target in the partitions; (d) detecting a signal from a label of the probe while the label is contained by the partitions; and (e) determining a number of partitions that are positive for the at least one first allelic form, or a number of partitions that are negative for the at least one first allelic form, based on the signal.

Paragraph C1. A method of detecting an allelic form of a target, the method comprising: (a) preparing a reaction mixture containing (i) at least one first allelic form and a second allelic form of a target, (ii) a same probe capable of binding specifically to each allelic form of the target, and (iii) a competitor configured to bind selectively to the at least one first allelic form relative to the second allelic form and to block binding of the probe to the second allelic form; (b) amplifying the at least one first allelic form of the target in at least a portion of the reaction mixture; (c) detecting a signal from a label of the probe; and (d) determining a level of the at least one first allelic form based on the signal.

Paragraph C2. The method of paragraph C1, wherein the step of detecting a signal includes a step of detecting a signal before the step of amplifying has been completed.

Paragraph C3. The method of paragraph C2, wherein the step of amplifying includes a step of exposing the reaction mixture to a plurality of thermal cycles, and wherein the step of detecting a signal is performed during and/or after each of two or more of the thermal cycles.

Paragraph C4. The method of paragraph C3, wherein the step of determining a level is based on a relationship between the signal and a number of the thermal cycles performed.

Paragraph C5. The method of any of paragraphs C1 to C4, wherein the steps of amplifying, detecting, and determining comprise a real-time PCR assay.

Paragraph C6. The method of any of paragraphs C1 to C5, wherein the probe is capable of binding specifically to each of the first and second allelic forms of the target below a melting temperature (interchangeably called a hybridization temperature).

Paragraph C7. The method of paragraph C6, wherein the step of amplifying is performed at least in part below the melting temperature.

Paragraph C8. The method of paragraph C6 or C7, wherein the step of amplifying includes a step of annealing at least one primer to the first and second allelic forms of the target and a step of extending the at least one primer after the step of annealing, and wherein the step of annealing is performed below the melting temperature.

Paragraph C9. The method of any of paragraphs C6 to C8, wherein the step of amplifying includes a step of extending at least one primer that is hybridized to the first and second allelic forms of the target, and wherein the step of extending is performed below the melting temperature.

Paragraph C10. The method of any of paragraphs C6 to C9, wherein the step of detecting is performed with the at least a portion of the reaction mixture below the melting temperature.

Paragraph C11. The method of paragraph C6, wherein the step of amplifying is performed entirely above the melting temperature.

Paragraph C12, The method of paragraph C11, wherein the step of amplifying includes a step of thermocycling the partitions through multiple thermal cycles, and wherein the partitions are above the melting temperature throughout each of the thermal cycles.

Paragraph D1. A composition, comprising: a plurality of isolated partitions collectively containing at least one first allelic form and a second allelic form of a target, each partition containing (a) a same probe capable of binding specifically to each of the first and second allelic forms of the target, (b) a competitor configured to bind selectively to the second allelic form relative to the at least one first allelic form and to block binding of the probe to the second allelic form, and (c) reagents to amplify the at least one first allelic form of the target.

Paragraph D2. The composition of paragraph D1, wherein the reagents include a same pair of primers to prime amplification of each allelic of the target.

Paragraph D3. The composition of paragraph D1 or D2, wherein each partition of a plurality of the partitions do not contain the at least one first allelic form of the target.

Paragraph D4. The composition of any of paragraphs D1 to D3, wherein each partition of a plurality of the partitions do not contain either form of the target.

Paragraph D5. The composition of any of paragraphs D1 to D4, wherein each partition of a plurality of the partitions contains at least one copy of the at least one first allelic form and at least one copy of the second allelic form.

Paragraph D6. The composition of any of paragraphs D1 to D5, wherein the probe and the competitor are each labeled with a photoluminophore.

Paragraph D7. The composition of paragraph D6, wherein the photoluminophore is a fluorophore.

Paragraph D8. The composition of paragraph D6 or paragraph D7, wherein the probe and the competitor are each labeled with a same photoluminophore.

Paragraph D9. The composition of paragraph D6 or paragraph D7, wherein the probe and the competitor are labeled with different photoluminophores relative to one another.

Paragraph D10. The composition of any of paragraphs D1 to D9, wherein each partition contains a polymerase.

Paragraph D11. The composition of paragraph D10, wherein the polymerase is a heat-stable polymerase.

Paragraph D12. The composition of any of paragraphs D1 to D11, wherein the partitions are droplets disposed in an immiscible carrier fluid.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of detecting an allelic form of a target, the method comprising:
preparing a mixture including (i) at least one first allelic form of a target and a second allelic form of the target, (ii) a same probe capable of binding specifically to each of the first and second allelic forms of the target, and (iii) a competitor that binds selectively to the second allelic form relative to the at least one first allelic form, wherein binding of the competitor to the second allelic form blocks binding of the probe to the second allelic form;
dividing at least a portion of the mixture into partitions, wherein each partition of only a subset of the partitions contains a first allelic form of the target;
amplifying the at least one first allelic form of the target in the partitions;
detecting a signal from a label of the probe while the label is contained by the partitions; and
determining a number of partitions that are positive for the at least one first allelic form, or a number of partitions that are negative for the at least one first allelic form, based on the signal.

2. The method of claim 1, wherein the probe and the competitor are complementary to partially overlapping regions of the second allelic form of the target.

3. The method of claim 1, wherein the at least one first allelic form includes a first allelic form having a deletion of two or more nucleotides relative to the second allelic form within a region that is complementary to the competitor.

4. The method of claim 1, further comprising a step of obtaining a level of the at least one first allelic form based on the number determined.

5. The method of claim 4, wherein the step of obtaining includes a step of obtaining a relative copy number of the at least one first allelic form.

6. The method of claim 5, wherein the relative copy number is relative to the second allelic form or a reference that is not a form of the target.

7. The method of claim 5, wherein the partitions are a first set of partitions created from a first mixture containing a portion of a sample that includes the first and second allelic forms of the target, further comprising a step of creating a second set of partitions from a second mixture containing a portion of the sample, wherein the number is determined from the first set, and wherein the step of obtaining a relative copy number is based on the number determined from the first set, and on a number of partitions of the second set that are positive for the second allelic form or a reference, or a number of partitions of the second set that are negative for the second allelic form or a reference.

8. The method of claim 7, wherein the at least one first allelic form is one or more variant forms of the target, wherein the second allelic form is a wild-type form of the target, and wherein the sample is more dilute in the second set of partitions than in the first set of partitions.

9. The method of claim 1, the probe being a first probe, wherein the competitor is a second probe, wherein the step of detecting a signal includes a step of detecting one or more signals from a label of the first probe and a label of the second probe, further comprising a step of determining a number of partitions that are positive for the second allelic form, or a number of partitions that are negative for the second allelic form based on at least one of the one or more signals.

10. The method of claim 9, further comprising a step of obtaining a level of the second allelic form based on the number determined for the second allelic form.

11. The method of claim 10, further comprising a step of determining a relative copy number of the at least one first allelic form, wherein the step of determining a relative copy number includes a step of obtaining a level of the at least one first allelic form and a level of the second allelic form based on a Poisson algorithm, and a step of comparing the level of the at least one first allelic form and the level of the second allelic form with one another.

12. The method of claim 1, wherein a melting temperature of the competitor hybridized with the second allelic form of the target is greater than a melting temperature of the probe hybridized with the second allelic form of the target.

13. The method of claim 1, wherein each partition when created contains more of the competitor than the probe on a molar basis.

14. The method claim 1, wherein the step of amplifying includes a step of amplifying each allelic form of the target with the same pair of primers.

15. The method of claim 1, wherein the partitions are droplets.

16. The method of claim 1, wherein the step of amplifying degrades at least a molar fraction of the competitor.

17. The method of claim 1, wherein the step of amplifying is catalyzed by a polymerase that catalyzes degradation of at least a molar fraction of the probe during the step of amplifying, and wherein the competitor is resistant to degradation catalyzed by the polymerase, such that amplification of the second allelic form of the target is blocked by the competitor.

18. A method of detecting an allelic form of a target, the method comprising:
   preparing a reaction mixture containing (i) at least one first allelic form and a second allelic form of a target, (ii) a same probe capable of binding specifically to each of the allelic forms of the target, and (iii) a competitor that binds selectively to the at least one first allelic form relative to the second allelic form, wherein binding of the competitor to the second allelic form blocks binding of the probe to the second allelic form;
   amplifying the at least one first allelic form of the target in at least a portion of the reaction mixture;
   detecting a signal from a label of the probe; and
   determining a level of the at least one first allelic form based on the signal.

19. The method of claim 18, wherein the steps of amplifying, detecting, and determining comprise a real-time PCR assay.

* * * * *

SEQUENCE LISTING

<160> NUMBER OF SEQ ID NOS: 20

<210> SEQ ID NO 1
<211> LENGTH: 60
<212> TYPE: DNA
<213> ORGANISM: Homo sapiens

<400> SEQUENCE: 1
aagttaaaat tcccgtcgct atcaaggaat taagagaagc aacatctccg aaagccaaca    60

<210> SEQ ID NO 2
<211> LENGTH: 28
<212> TYPE: DNA
<213> ORGANISM: Homo sapiens

<400> SEQUENCE: 2
cgtcgctatc aaggaattaa gagaagca    28

<210> SEQ ID NO 3
<211> LENGTH: 18
<212> TYPE: DNA
<213> ORGANISM: Homo sapiens

-continued

<400> SEQUENCE: 3
aattcccgtc gctatcaa                                                          18

<210> SEQ ID NO 4
<211> LENGTH: 45
<212> TYPE: DNA
<213> ORGANISM: Homo sapiens

<400> SEQUENCE: 4
aagttaaaat tcccgtcgct atcaaaacat ctccgaaagc caaca                            45

<210> SEQ ID NO 5
<211> LENGTH: 45
<212> TYPE: DNA
<213> ORGANISM: Homo sapiens

<400> SEQUENCE: 5
aagttaaaat tcccgtcgct atcaaaatat ctccgaaagc caaca                            45

<210> SEQ ID NO 6
<211> LENGTH: 45
<212> TYPE: DNA
<213> ORGANISM: Homo sapiens

<400> SEQUENCE: 6
aagttaaaat tcccgtcgct atcaagacat ctccgaaagc caaca                            45

<210> SEQ ID NO 7
<211> LENGTH: 42
<212> TYPE: DNA
<213> ORGANISM: Homo sapiens

<400> SEQUENCE: 7
aagttaaaat tcccgtcgct atcaaggttc cgaaagccaa ca                               42

<210> SEQ ID NO 8
<211> LENGTH: 42
<212> TYPE: DNA
<213> ORGANISM: Homo sapiens

<400> SEQUENCE: 8
aagttaaaat tcccgtcgct atcaaggatc cgaaagccaa ca                               42

<210> SEQ ID NO 9
<211> LENGTH: 51
<212> TYPE: DNA
<213> ORGANISM: Homo sapiens

<400> SEQUENCE: 9
aagttaaaat tcccgtcgct atcaaggagc caacatctcc gaaagccaac a                     51

<210> SEQ ID NO 10
<211> LENGTH: 48
<212> TYPE: DNA
<213> ORGANISM: Homo sapiens

<400> SEQUENCE: 10
aagttaaaat tcccgtcgct atcaaggagc aatctccgaa agccaaca                         48

<210> SEQ ID NO 11
<211> LENGTH: 45
<212> TYPE: DNA

<213> ORGANISM: Homo sapiens

<400> SEQUENCE: 11
aagttaaaat tcccgtcgct atcaaggaat ctccgaaagc caaca          45

<210> SEQ ID NO 12
<211> LENGTH: 42
<212> TYPE: DNA
<213> ORGANISM: Homo sapiens

<400> SEQUENCE: 12
aagttaaaat tcccgtcgct atcaaggaac cgaaagccaa ca             42

<210> SEQ ID NO 13
<211> LENGTH: 51
<212> TYPE: DNA
<213> ORGANISM: Homo sapiens

<400> SEQUENCE: 13
aagttaaaat tcccgtcgct atcaaggaac caacatctcc gaaagccaac a   51

<210> SEQ ID NO 14
<211> LENGTH: 48
<212> TYPE: DNA
<213> ORGANISM: Homo sapiens

<400> SEQUENCE: 14
aagttaaaat tcccgtcgct atcaaggaac catctccgaa agccaaca       48

<210> SEQ ID NO 15
<211> LENGTH: 42
<212> TYPE: DNA
<213> ORGANISM: Homo sapiens

<400> SEQUENCE: 15
aagttaaaat tcccgtcgct atcaaggaac agaaagccaa ca             42

<210> SEQ ID NO 16
<211> LENGTH: 45
<212> TYPE: DNA
<213> ORGANISM: Homo sapiens

<400> SEQUENCE: 16
aagttaaaat tcccgtcgct atcaaggaat ctccgaaagc caaca          45

<210> SEQ ID NO 17
<211> LENGTH: 42
<212> TYPE: DNA
<213> ORGANISM: Homo sapiens

<400> SEQUENCE: 17
aagttaaaat tcccgtcgct atcaaggaat cgaaagccaa ca             42

<210> SEQ ID NO 18
<211> LENGTH: 92
<212> TYPE: DNA
<213> ORGANISM: Homo sapiens

<400> SEQUENCE: 18
ggatcccaga aggtgagaaa gttaaaattc ccgtcgctat caaggaatta agagaagcaa   60
catctccgaa agccaacaag gaaatcctcg at                                92

```
<210> SEQ ID NO 19
<211> LENGTH: 17
<212> TYPE: DNA
<213> ORGANISM: Homo sapiens

<400> SEQUENCE: 19
ggatcccaga aggtgag                                                  17

<210> SEQ ID NO 20
<211> LENGTH: 19
<212> TYPE: DNA
<213> ORGANISM: Homo sapiens

<400> SEQUENCE: 20
atcgaggatt tccttgttg                                                19
```